US011517384B2

(12) United States Patent
Tojo et al.

(10) Patent No.: US 11,517,384 B2
(45) Date of Patent: Dec. 6, 2022

(54) SURGICAL SYSTEM AND METHOD FOR CONTROLLING THE SAME

(71) Applicants: KAWASAKI JUKOGYO KABUSHIKI KAISHA, Kobe (JP); MEDICAROID CORPORATION, Kobe (JP)

(72) Inventors: Tsuyoshi Tojo, Ibaraki (JP); Kenji Noguchi, Kobe (JP); Tetsushi Ito, Kobe (JP); Tetsuya Nakanishi, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 845 days.

(21) Appl. No.: 16/396,836

(22) Filed: Apr. 29, 2019

(65) Prior Publication Data

US 2019/0328472 A1   Oct. 31, 2019

(30) Foreign Application Priority Data

Apr. 27, 2018   (JP) .............................. JP2018-086896

(51) Int. Cl.

| A61B 34/37 | (2016.01) |
|---|---|
| A61B 17/34 | (2006.01) |
| A61B 1/00 | (2006.01) |
| A61B 1/05 | (2006.01) |

(Continued)

(52) U.S. Cl.
CPC .......... *A61B 34/37* (2016.02); *A61B 1/00006* (2013.01); *A61B 1/00045* (2013.01); *A61B 1/00149* (2013.01); *A61B 1/05* (2013.01); *A61B 1/3132* (2013.01); *A61B 17/3423* (2013.01); *A61B 2017/3447* (2013.01); *A61B 2034/301* (2016.02); *A61B 2034/302* (2016.02)

(58) Field of Classification Search
CPC ....................... A61B 1/00006; A61B 1/00149
USPC ......................................................... 600/102
See application file for complete search history.

(56) References Cited

U.S. PATENT DOCUMENTS

| 8,029,516 B2 | 10/2011 | Mohr et al. | |
|---|---|---|---|
| 2005/0234293 A1* | 10/2005 | Yamamoto | ............. A61B 90/57 600/102 |

(Continued)

FOREIGN PATENT DOCUMENTS

JP   2016-530004 A   9/2016

*Primary Examiner* — Ryan N Henderson
*Assistant Examiner* — Pamela F Wu
(74) *Attorney, Agent, or Firm* — Oliff PLC

(57) ABSTRACT

A surgical system includes a surgical assist robot including a robot main body and a slave controller, and a console. The robot main body has an entry guide, an entry guide support device, and at least one manipulator having an end effector provided at a distal end. The entry guide includes an inner cylinder, an outer cylinder into which the inner cylinder is inserted in an insertion axial direction, and a guide advancing device that displaces the inner cylinder in the insertion axial direction with respect to the outer cylinder. While a position and a posture of the end effector that has advanced from the entry guide are maintained, the inner cylinder is caused to advance toward the end effector within a predetermined movable range along the insertion axial direction with respect to the outer cylinder.

18 Claims, 11 Drawing Sheets

(51) Int. Cl.
  *A61B 1/313* (2006.01)
  *A61B 34/30* (2016.01)

(56) References Cited

U.S. PATENT DOCUMENTS

| | | | |
|---|---|---|---|
| 2008/0234631 A1* | 9/2008 | Reis | A61B 34/37 |
| | | | 604/122 |
| 2016/0199138 A1 | 7/2016 | Cooper et al. | |
| 2017/0086931 A1* | 3/2017 | Auld | A61B 34/37 |
| 2017/0143435 A1* | 5/2017 | Scholan | H01L 27/11519 |
| 2019/0231450 A1* | 8/2019 | Waterbury | A61B 17/0281 |

* cited by examiner

SURGICAL SYSTEM AND METHOD FOR CONTROLLING THE SAME

CROSS-REFERENCE TO RELATED APPLICATIONS

This application claims priority based on Japanese Patent Application No. 2018-086896 filed on Apr. 27, 2018, the entire disclosure of which is incorporated herein.

BACKGROUND OF THE INVENTION

(1) Field of the Invention

The present invention relates to a surgical system including a master-slave type surgical assist robot.

(2) Description of Related Art

Conventionally, a surgical system including a master-slave type surgical assist robot has been known. In surgery using a surgical system, a surgeon remotely controls the operation of a surgical assist robot using a console, and the surgical assist robot performs surgery on a surgery site of a patient. For example, JP2016-530004A discloses this type of a surgical system.

A teleoperated surgical system described in JP2016-530004A is for performing single incision laparoscopic surgery. The teleoperated surgical system includes a patient cart (corresponding to a surgical assist robot) and a surgeon console. The patient cart includes a plurality of surgical device assemblies supported by a manipulator. The surgical device assembly includes an instrument including a surgical instrument and a movable wrist, a drive unit for the instrument, and a sterile adapter connecting them.

Further, a surgical assist robot described in U.S. Pat. No. 8,029,516 B2 includes a plurality of instruments bundled by being inserted into an entry guide (tool guide) inserted into a body wall of a patient, and an image capture device. The entry guide is supported by a guide holder on a robotic arm assembly supported by a patient cart.

SUMMARY OF THE INVENTION

In a surgical assist robot shown in JP2016-530004A and U.S. Pat. No. 8,029,516B2, a plurality of surgical instruments and an endoscope are bundled by being inserted into a single entry guide ted in a body surface of a patient, and a mutual positional relationship is also maintained. A manipulator arm connected to the surgical instrument is extremely thin and therefore has low rigidity. Therefore, if an advancing amount of the surgical instrument from the entry guide becomes large, a portion of the manipulator arm connected to the surgical instrument that has advanced from the entry guide is deformed or shaken, and accuracy in a position and a posture of the surgical instrument or the endoscope may be lowered.

The present invention has been made in view of the above circumstances, and an object of the present invention is to reduce deformation and shaking of a manipulator having a surgical instrument or an endoscopic camera at a distal end to improve positional accuracy of the surgical instrument and the endoscopic camera in a surgical system for single incision laparoscopic surgery.

The surgical system according to an aspect of the present invention includes a surgical assist robot having a robot main body and a slave controller, and a console that is communicably connected to the slave controller and configured to acquire input from a surgeon and transmit a command corresponding to the input to the slave controller.

The robot main body has an entry guide including an inner cylinder provided with a plurality of parallel guide bores extending in an insertion axial direction, an outer cylinder in which the inner cylinder is inserted in the insertion axial direction, and a guide advancing device configured to displace the inner cylinder in the insertion axial direction with respect to the outer cylinder, an entry guide support device configured to support the entry guide, an instrument manipulator that has a surgical instrument provided at a distal end and is inserted into one of the guide bores, and an endoscope manipulator that has an endoscopic camera provided at a distal end and is inserted into another one of the guide bores.

The slave controller controls the robot main body to perform an entry guide advancing operation for causing the inner cylinder to advance into a body cavity of a patient within a predetermined movable range along the insertion axial direction with respect to the outer cylinder while a position and a posture of the endoscopic camera and the surgical instrument that have advanced into the body cavity from the entry guide are maintained.

Further, the method for controlling a surgical system according to an aspect of the present invention is a method for controlling a surgical system including a surgical assist robot including a robot main body and a console that receives input by a surgeon. The robot main body has: an entry guide including an inner cylinder extending in an insertion axial direction, an outer cylinder in which the inner cylinder is inserted in the insertion axial direction, and a guide advancing device configured to displace the inner cylinder in the insertion axial direction with respect to the outer cylinder; an entry guide support device configured to support the entry guide; and at least one manipulator that has an end effector provided at a distal end and is inserted into the inner cylinder. The method includes the steps of: receiving input of a body cavity insertion manipulation via the console; operating the manipulator, such that the end effector advances from the entry guide, in response to the body cavity insertion command; and operating the entry guide to perform entry guide advancing operation, in which the inner cylinder is caused to advance toward the end effector within a predetermined movable range along the insertion axial direction with respect to the outer cylinder while a position and a posture of the end effector that has advanced from the entry guide are maintained.

According to the surgical system and method for controlling the surgical system, the distal end of the instrument manipulator and the endoscope manipulator and the distal end of the entry guide (that is, the distal end of the inner cylinder) approach by the entry guide advancing operation. In other words, a length of the instrument manipulator and the endoscope manipulator extending from an exit of the entry guide is shortened. Therefore, shaking and deformation of the portion of the instrument manipulator and the endoscope manipulator which advances from the exit of the entry guide can be reduced, and the positional accuracy of the surgical instrument and the endoscopic camera can be improved.

The above object, other objects, features, and advantages of the present invention will be apparent from the following detailed description of the preferred implementation taken in conjunction with the accompanying drawings.

DETAILED DESCRIPTION OF PREFERRED EMBODIMENTS

Figure 1:
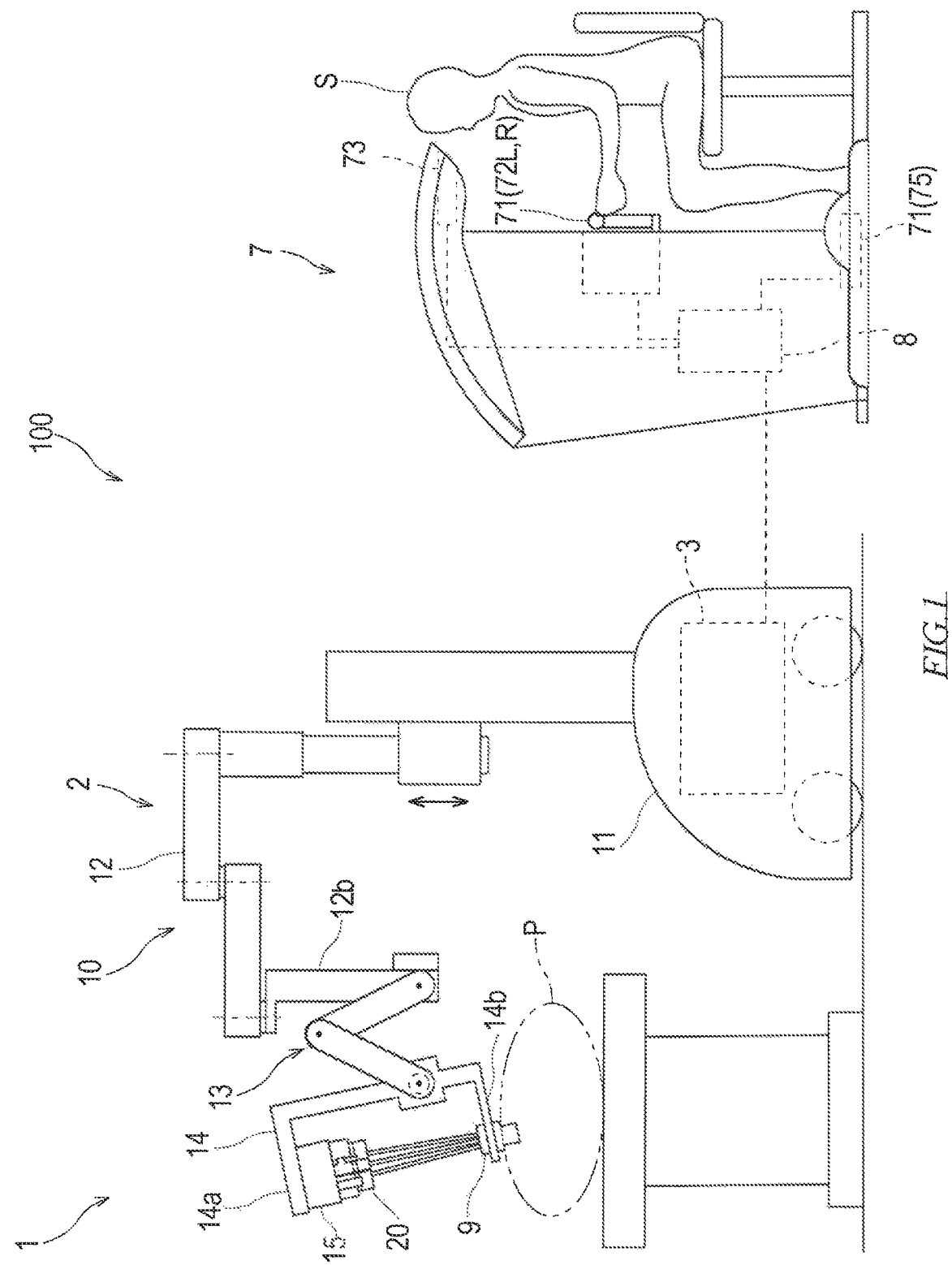
FIG. 1 is a diagram showing an overall schematic configuration of a surgical system according to an embodiment of the present invention.

Next, embodiments of the present invention will be described with reference to the drawings. FIG. 1 is a diagram showing an overall schematic configuration of a surgical system 100 according to an embodiment of the present invention. The surgical system 100 shown in FIG. 1 is for performing single incision laparoscopic surgery, and includes a surgical assist robot 1 and a console 7. Hereinafter, each constituent of the surgical system 100 will be described in detail.

[Surgical Assist Robot 1]

The surgical assist robot 1 constitutes an interface between the surgical system. 100 and a patient P. The surgical assist robot 1 is placed beside the operating table on which the patient P lies in an operating room which is a sterile field.

The surgical assist robot 1 includes a robot main body 2 and a slave controller 3. The robot main body 2 includes a plurality of surgery manipulators 20, a single entry guide 9, and a positioner 10 for positioning the surgery manipulator 20 and the entry guide 9 on the patient P.

(Entry Guide 9)

Figure 2:
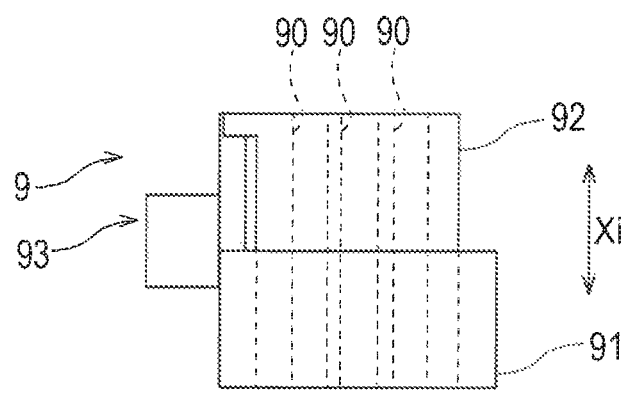
FIG. 2 is a side view of an entry guide.
Figure 3:
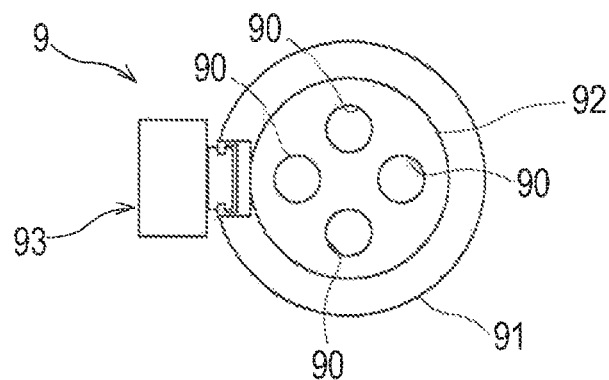
FIG. 3 is a plan view of the entry guide.

The entry guide 9 is attached to a cannula (not shown) placed on a body sur ace of the patient P. FIG. 2 is a side view of the entry guide 9, and FIG. 3 is a plan view of the entry guide 9. The entry guide 9 shown in FIGS. 2 and 3 includes an outer cylinder 91, an inner cylinder 92, and a guide advancing device 93.

The outer cylinder 91 is a tubular body extending in an insertion axial direction Xi. The outer cylinder 91 is held by an entry guide support portion 14b of the positioner 10 described later. Therefore, a position and a posture of the outer cylinder 91 are changed by operation of the positioner 10.

The inner cylinder 92 is a tubular body or a cylindrical body extending in the insertion axial direction Xi, and is concentrically inserted in the outer cylinder 91. The inner cylinder 92 has a plurality of guide bores 90 penetrating the inner cylinder 92 in the insertion axial direction Xi. The plurality of guide bores 90 are arranged in parallel. The surgery manipulators 20 are individually inserted into the guide bores 90.

The guide advancing device 93 is a linear motion device that displaces the inner cylinder 92 in the insertion axial direction Xi with respect to the outer cylinder 91. In the present embodiment, the guide advancing device 93 is a motorized linear slider including a drive unit and a rail that are provided in the outer cylinder 91 and a slider provided in the inner cylinder 92. However, the guide advancing device 93 is not limited to the present embodiment. As the guide advancing device 93, a known linear motion device, such as a motorized or hydraulic linear slider, a motorized rack and pinion, or a motorized or hydraulic cylinder, can be employed.

(Positioner 10)

Returning to FIG. 1, the positioner 10 has a function as an entry guide support device that supports the entry guide 9. The positioner 10 includes a horizontal articulated manipulator 12 supported by a carriage 11, a support member 12b provided at a distal end of the horizontal articulated manipulator 12, a vertical articulated manipulator 13 supported by the horizontal articulated manipulator 12 via the support member 12b, and a support frame 14 provided at a distal end of the vertical articulated manipulator 13. However, the configuration of the positioner 10 is not limited to the present embodiment, and may be any configuration as long as the configuration allows the entry guide 9 to be positioned at a target position and in a target posture with excellent accuracy. The positioner 10 is described, for example, in JP-A-2017-104453, which is incorporated herein by reference.

The support frame 14 has a channel shape, and has one end and the other end facing each other with space therebetween. At one end of the support frame 14, an entry guide support portion 14b for supporting the entry guide 9 is provided. Further, at the other end of the support frame 14, a surgery manipulator support portion 14a is provided. Relative positions of the surgery manipulator support portion 14a and the entry guide support portion 14b may be variable or constant.

The surgery manipulator support portion 14a is provided with a support block 15 for collectively supporting the plurality of the surgery manipulators 20. The plurality of the surgery manipulators 20 each include an instrument manipulator 21 having a surgical instrument 28 and an endoscope manipulator 31 having an endoscopic camera 33.

(Instrument Manipulator 21)

Figure 4:
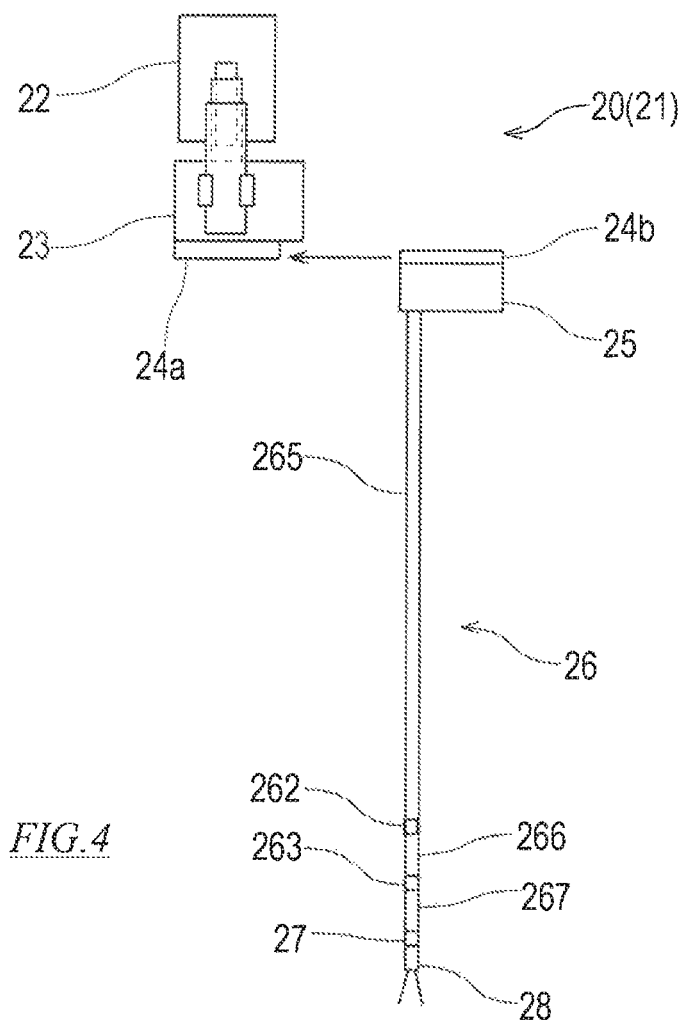
FIG. 4 is a diagram showing an example of an instrument manipulator having a surgical instrument.

FIG. 4 is a diagram showing an example of the instrument manipulator 21 having a surgical instrument 28. The instrument manipulator 21 shown in FIG. 4 includes a translation unit 22, a drive unit 23, a transmission unit 25, an elongated hollow shaft-like arm 26, a wrist 27, and the surgical instrument 28 as an end effector, which are connected in sequence from a proximal end toward a distal end.

The translation unit 22 forms a translational joint in the instrument manipulator 21. The translation unit 22 is what is called a linear motion device, and may be, for example, a motorized linear slide cylinder. The translation unit 22 is fixed to the support block 15. The drive unit 23 is attached to a slider of the translation unit 22. The transmission unit 25, the arm 26, the wrist 27, and the surgical instrument 28 are integrally configured, and the transmission unit 25 is detachably connected to the drive unit 23 with adapters 24a and 24b interposed therebetween.

The operation of the translation unit 22 causes portions of the instrument manipulator 21 other than the translation unit 22 to move in parallel with the insertion axial direction Xi of the entry guide 9. By such a translational movement of the instrument manipulator 21, a distal portion including the arm 26 of the instrument manipulator 21, the wrist 27 and the surgical instrument 28 can be inserted into the guide bore 90 of the entry guide 9, and a distal portion of the instrument manipulator 21 inserted into the guide bore 90 can be caused to advance into or be retracted from a body cavity of the patient P.

Figure 5:
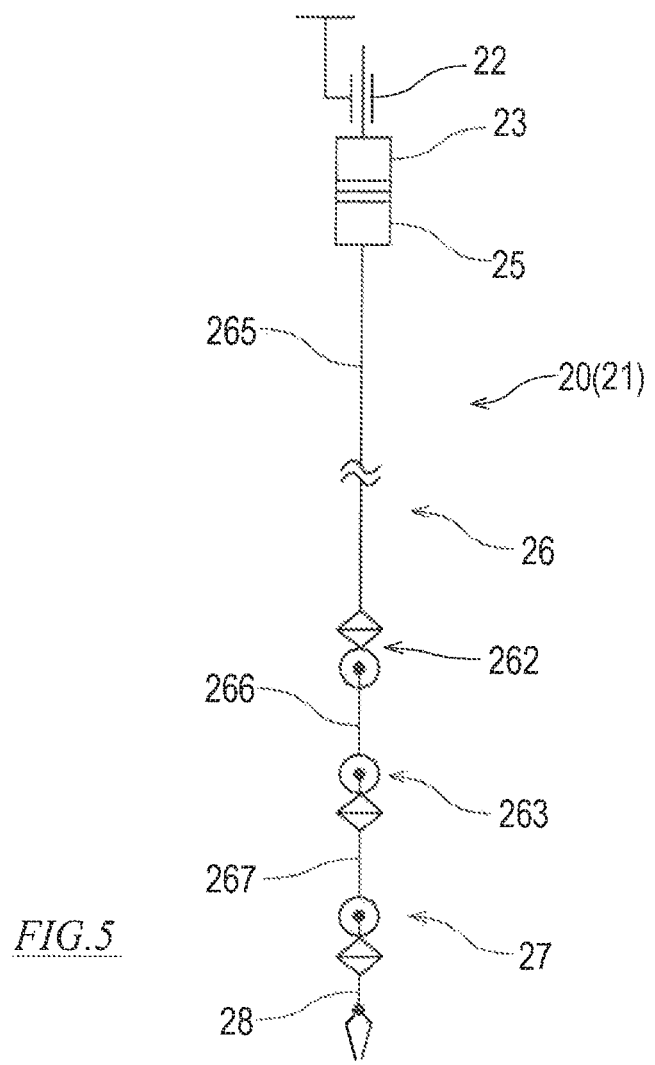
FIG. 5 is a diagram for describing a joint configuration of the instrument manipulator.

The arm 26 includes a proximal link 265, a middle link 266, and a distal link 267 connected in sequence from a distal side. These links are comprised of a substantially hollow straight pipe. As shown in FIG. 5, the proximal link 265 and the middle link 266 are connected by a shoulder 262 including a twisting joint and a bending joint. The middle link 266 and the distal link 267 are connected by an elbow 263 including a bending joint.

Returning to FIG. 4, a distal end of the arm 26 is connected to a proximal end of the wrist 27. The distal end of the wrist 27 is connected to the proximal end of the surgical instrument 28. As shown in FIG. 5, the wrist 27 includes a bending joint and a twisting joint sequentially connected from the distal side.

The elbow 263 and the shoulder 262 may interlock such that the proximal link 265 and the distal link 267 remain parallel. A mechanism for interlocking the elbow 263 and the shoulder 262 is described in US 2017/056118 A1, which is incorporated herein by reference. Alternatively, the elbow 263 and the shoulder 262 may operate independently, causing the proximal link 265 and the distal link 267 to be non-parallel.

The bending joints included in the arm 26 and the wrist 27 may be obtained by, for example, a plurality of plate-shaped segments arranged in series in a thickness direction and a manipulation cable inserted in the thickness direction across the plurality of segments. Such a bending joint is described, for example, in International Publication WO2017/006373A1, which is incorporated herein by reference. However, the bending joint included in the arm 26 and the wrist 27 is not limited to the above configuration, and a publicly-known bending joint structure may be employed.

The twisting joint included in the arm 26 and the wrist 27 may be obtained by, for example, an inner and outer double cylinder and a manipulation cable for rotating the inner cylinder with respect to the outer cylinder. Such a twisting joint is described, for example, in International Publication WO2017/006374 A1, which is hereby incorporated by reference. However, the twisting joint included in the arm 26 and the wrist 27 is not limited to the above configuration, and a publicly-known twisting joint structure may be employed.

The surgical instrument 28 means an actual manipulated part which is inserted at a surgical site in the abdominal cavity of the patient P and can be driven from the outside of the abdominal cavity to perform desired treatment or a medical function of a target tissue at the surgical site. The surgical instrument 28 may be a surgical instrument, such as a forceps, a grasper, scissors, a stapler, a needle holder, an electrosurgical knife, and the like. Further, the surgical instrument 28 may also be an electrically driven device, such as an electrosurgical electrode, a transducer, a sensor, or the like. Further, the surgical instrument 28 may be a nozzle for supplying fluid for suction, gas injection, cleaning, a treatment fluid, accessory introduction, biopsy and removal, and the like.

The wrist 27 and the area 26 are hollow, and manipulation cables and various cables of the surgical instrument 28, the wrist 27, and the arm 26 extend through the wrist 27 and the arm 26 to the transmission unit 25. The transmission unit 25 is provided with a drive disk (not shown) in which a manipulation cable is wound around each manipulation cable. Torque is transmitted to each drive disk from a drive source (not shown) such as a servomotor provided in the drive unit 23 via the adapters 24a and 24b. The manipulation cable is loosened or pulled by the rotation of the drive disk, so that the surgical instrument 28, the wrist 27, and the arm 26 operate.

(Endoscope Manipulator 31)

Figure 6:
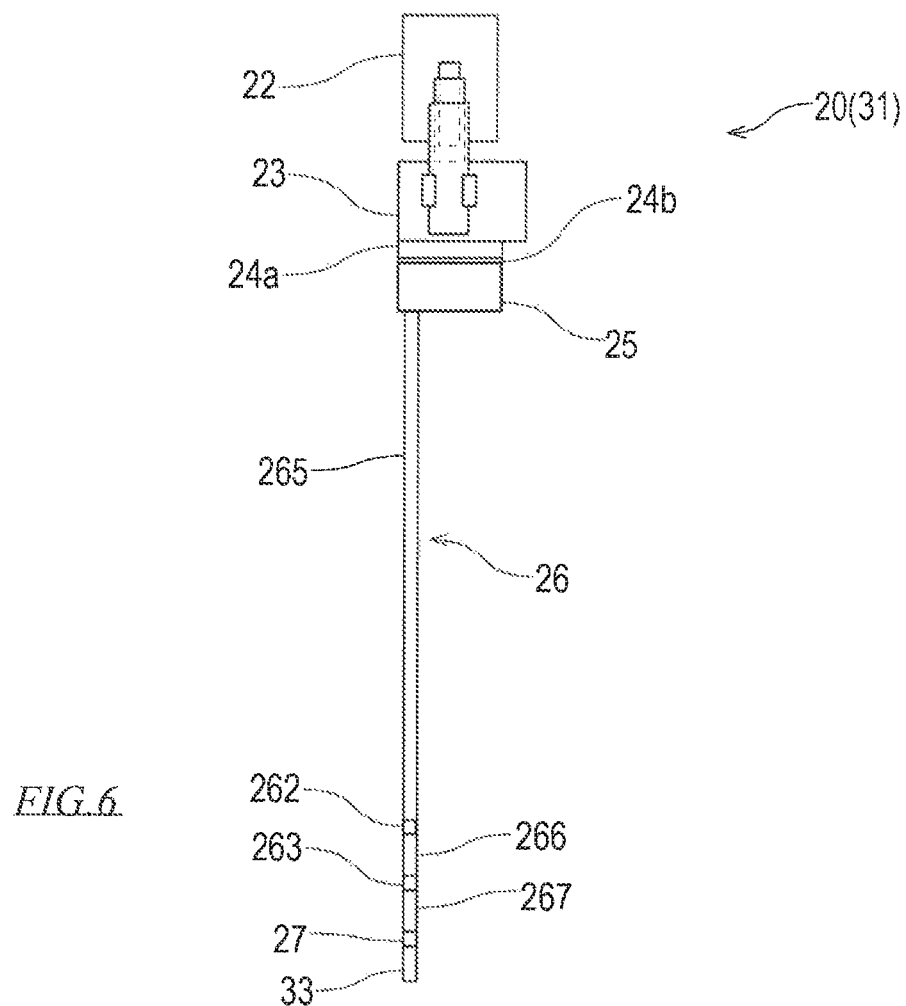
FIG. 6 is a diagram showing an example of an endoscope manipulator having an endoscopic camera.

FIG. 6 is a diagram showing an example of an endoscope manipulator 31 having an endoscopic camera 33. The endoscope manipulator 31 shown in FIG. 6 has, as an end effector, the endoscopic camera 33 including an objective lens and a light guide at a distal end.

The endoscope manipulator 31 has a substantially similar configuration as the instrument manipulator 21 except for the surgical instrument 28 provided at the distal end. That is, in the above description of the instrument manipulator 21, the configuration of the endoscope manipulator 31 can be described by replacing the surgical instrument 28 provided at the distal end with the endoscopic camera 33. From the above, the detailed description of the configuration of the endoscope manipulator 31 will be omitted by referring to the description of the instrument manipulator 21 and attaching the same reference numerals to elements corresponding to the instrument manipulator 21 in FIG. 6. Note that the surgical assist robot 1 according to the present embodiment has an axial structure in which the endoscope manipulator 31 and the instrument manipulator 21 are similar. However, the endoscope manipulator 31 has an axial structure different from that of the instrument manipulator 21.

(Slave Controller 3)

The slave controller 3 is communicably connected to the console 7. The slave controller 3 operates the robot main body 2 of the surgical assist robot 1 based on a command corresponding to the input received by the console 7. Further, the slave controller 3 transmits information to the console 7 so as to cause the console 7 to display an endoscope image of the endoscopic camera 33 or cause the console 7 to perform operation corresponding to operation of the robot main body 2.

The slave controller 3 is what is called a computer, and includes an arithmetic processing unit, such as a CPU, and a storage unit, such as a RUM and a RAM (all not shown). The storage unit stores a program executed by the arithmetic processing unit, various pieces of fixed data, and the like. The arithmetic processing unit performs data transmission and reception with other devices including the console 7. Further, the arithmetic processing unit performs input of detection signals from various sensors and output of control signals to each control target. In the slave controller 3, the arithmetic processing unit reads and executes software, such as a program, stored in the storage unit to perform processing for performing a function as the slave controller 3 described later. Note that the slave controller 3 may execute each processing by centralized control by a single computer, or may execute each processing by distributed control by cooperation of a plurality of computers. Further, the slave controller 3 may be configured with a microcontroller, a programmable logic controller (PLC), or the like.

The slave controller 3 has a positioner control function for controlling operation of the positioner 10 so as to position the entry guide 9 at a predetermined position and in a predetermined posture. The horizontal articulated manipulator 12 and the vertical articulated manipulator 13 of the positioner 10 include a servomotor provided for each joint, a rotation sensor for detecting a rotational position of each joint, and a drive it including a power transmission mechanism for transmitting power of the servomotor to a joint (all not shown).

The slave controller 3 has a surgical instrument control function for controlling operation of each of the instrument manipulators 21. More specifically, the slave controller 3 has a function of controlling operation of the surgical instrument 28 and a function of controlling operation of the instrument manipulator 21 so as to bring the surgical instrument 28 into a position and a posture corresponding to a command. Each of the instrument manipulators 21 include a servomotor provided for each joint, a rotation sensor for detecting a rotational position of a motor, and a drive unit including a power transmission mechanism for transmitting power of the servomotor to a joint (all not shown).

The slave controller 3 has an endoscope control function for controlling operation of the endoscope manipulator 31. More specifically, the slave controller 3 has a function of controlling operation of the endoscopic camera 33 and a function of controlling operation of the endoscope manipulator 31 so as to bring the endoscopic camera 33 into a position and a posture corresponding to a command. The endoscope manipulator 31 includes a servomotor provided for each joint, a rotation sensor for detecting a rotational position of a motor, and a drive unit including a power transmission mechanism for transmitting power of the servomotor to a joint (all not shown).

[Console 7]

The console 7 constitutes an interface between the surgical system 100 and a surgeon S, and is a device that receives input of a manipulation of the surgeon S to the surgical assist robot 1. The console 7 is installed beside an operating table or away from the operating table in an operating room or outside the operating room.

Figure 7:
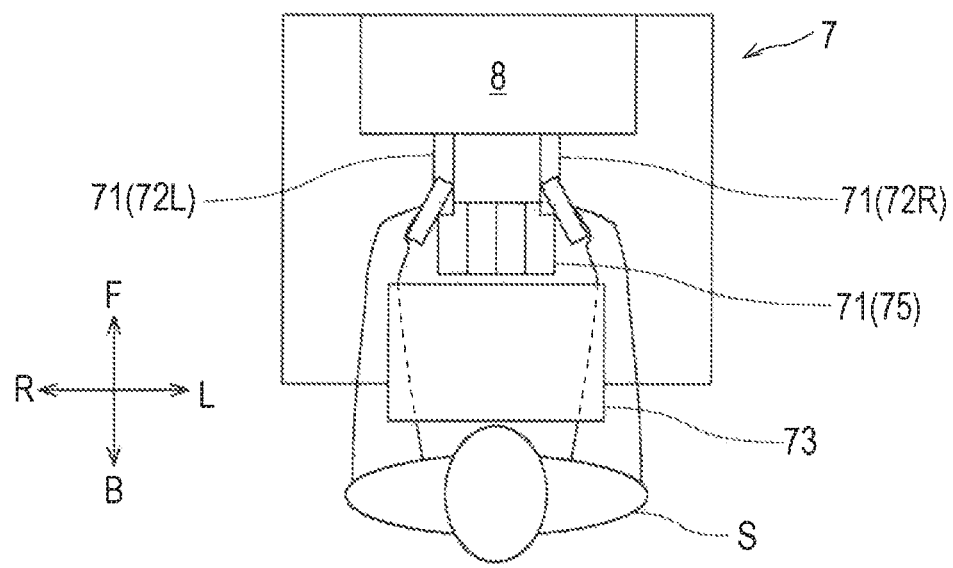
FIG. 7 is a plan view of a console.

FIG. 7 is a plan view of the console 7. The console 7 shown in FIG. 7 includes a manipulation input device 71 that receives input of a manipulation from the surgeon S, a display device 73 that displays an image captured by the endoscopic camera 33, and a master controller 8. Similar to the slave controller 3, the master controller 8 may be configured with a computer and the like. The manipulation input device 71 includes a pair of left and right master manipulators 72L and 72R, and a manipulation pedal 75. The console 7 is described, for example, in JP-A-2017-189495, which is incorporated herein by reference. The manipulation input device 71 may further include publicly-known manipulation tools, such as a lever, a button, a touch panel, a joystick, and a motion capture, in addition to the master manipulators 72L and 72R and the manipulation pedal 75.

The pair of left and right master manipulators 72L and 72R have a manipulation unit provided at each distal end, and the surgeon S applies a load to the manipulators 72L and 72R from the manipulation unit. In the present embodiment, the master manipulators 72L and 72R are manipulation tools that receive input of manipulations regarding movements of a position and a posture of the endoscopic camera 33 and the surgical instrument 28. Further, the master manipulators 72L and 72R also function as a manipulation tool that receives input of manipulations regarding a movement of the entry guide 9 and input of manipulations regarding a movement of the endoscopic camera 33. Further, the manipulation pedal 75 is a manipulation tool that receives input of manipulations, such as zooming the endoscopic camera 33, switching control modes, and switching the instrument manipulator 21 associated with the pair of left and right master manipulators 72L and 72R.

[Operation Example of the Surgical System 100]

In the surgical system 100 configured as described above, a command corresponding to the input received by the console 7 is input to the slave controller 3. The slave controller 3 operates the robot main body 2 in a manner, for example, described below in response to the input received by the console 7.

(Positioning Operation of the Entry Guide 9)

In response to input of a positioning manipulation of the entry guide 9 received by the console 7, the slave controller 3 operates the positioner 10 so as to position the entry guide 9 at a predetermined position and in a predetermined posture with respect to a cannula placed on a body surface of the patient P. When the entry guide 9 is positioned, the plurality of surgery manipulators 20 are also automatically positioned.

(Body Cavity Insertion Operation of the Surgical Instrument 28)

In response to input of a body cavity insertion manipulation of the surgical instrument 28 received by the console 7, the slave controller 3 operates each of the translation units 22 such that the endoscopic camera 33 and the surgical instrument 28 are inserted into a body cavity through the entry guide 9. The slave controller 3 starts capturing by the endoscopic camera 33 at a predetermined timing at which the endoscopic camera 33 is inserted into the body cavity.

Figure 10A:
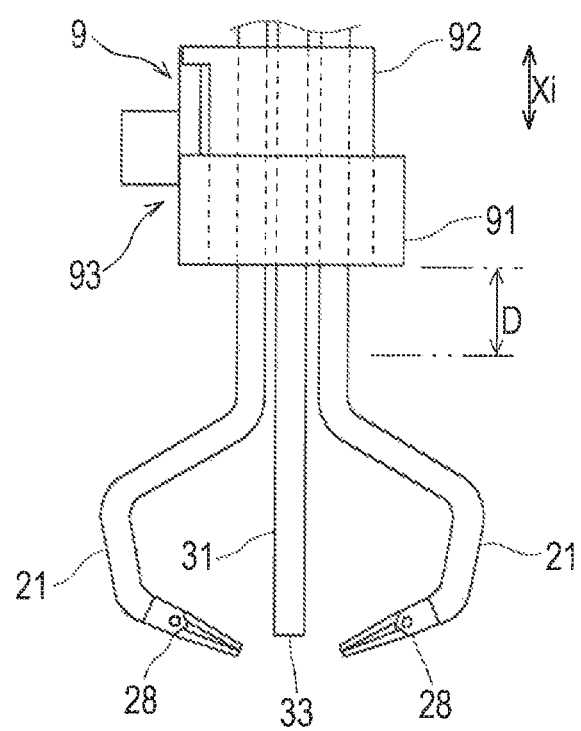
FIG. 10A is a diagram for describing a state in which an inner cylinder of the entry guide advances, showing a state in which the inner cylinder retreats.

FIG. 10A is a diagram showing a state in which the inner cylinder 92 of the entry guide 9 is retracted into the outer cylinder 91 at the time of body cavity insertion operation of the surgical instrument 28. As shown in FIG. 10A, at the time of the body cavity insertion operation of the surgical instrument 28, the instrument manipulator 21 operates to cause the surgical instrument 28 to advance from the entry guide 9 into a body cavity, and the endoscope manipulator 31 operates to cause the endoscopic camera 33 to advance from the entry guide 9 into a body cavity. Since the outer cylinder 91 of the entry guide 9 is supported by the support frame 14, at least part of the outer cylinder 91 is positioned outside a body surface of the patient P. In a case where a surgical site is sufficiently close to a body surface, a portion of the instrument manipulator 21 and the endoscope manipulator 31 restrained by the entry guide 9 is sufficiently close to a distal end where the surgical instrument 28 and the endoscopic camera 33 are located. Therefore, deformation and shaking of the instrument manipulator 21 and the endoscope manipulator 31 are suppressed to such an extent that the positional accuracy of the surgical instrument 28 and the endoscopic camera 33 is not impaired. However, as the surgical site is far from the body surface, portions of the instrument manipulator 21 and the endoscope manipulator 31 that advance from the entry guide 9 become longer. As a result, portions of the instrument manipulator 21 and the endoscope manipulator 31 restrained by the entry guide 9 become far from the distal end where the surgical instrument 28 and the endoscopic camera 33 are located, and deformation and shaking of the instrument manipulator 21 and the endoscope manipulator 31 become large.

Figure 10B:
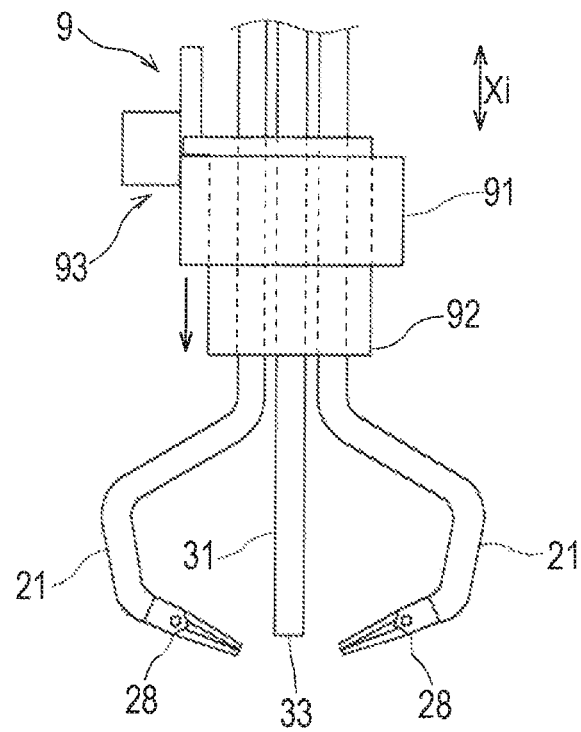
FIG. 10B is a diagram for describing a state in which the inner cylinder of the entry guide advances, showing a state in which the inner cylinder advances.

In view of the above, as shown in FIG. 10B, while positions and postures of the surgical instrument 28 and the endoscopic camera 33 that advance from the entry guide 9 are maintained, the inner cylinder 92 of the entry guide 9 is caused to advance toward the surgical instrument 28 and the endoscopic camera 33 side with respect to the outer cylinder 91 (this operation is referred to as "entry guide advancing operation"). In the entry guide advancing operation, the inner cylinder 92 moves relative to the instrument manipulator 21 and the endoscope manipulator 31 whose relative positions to the outer cylinder 91 are held. By this entry guide advancing operation, a portion of the instrument manipulator 21 and the endoscope manipulator 31 restrained by the entry guide 9 approaches to the distal end where the surgical instrument 28 and the endoscopic camera 33 are located. In this manner, deformation and shaking of the instrument manipulator 21 and the endoscope manipulator 31 are suppressed, and lowering in the positional accuracy of the surgical instrument 28 and the endoscopic camera 33 can be suppressed.

The entry guide advancing operation may be automatically controlled by the slave controller 3. In this case, when advancing amounts from the exit of the entry guide 9 (that is, advancing amounts from the distal end of the inner cylinder of both the endoscopic camera 33 and the surgical instrument 28 exceed a predetermined threshold, the slave controller 3 causes the guide advancing device 93 included in the robot main body 2 to perform the entry guide advancing operation. The threshold may be appropriately determined based on shapes of the instrument manipulator 21 and the endoscope manipulator 31.

A relative positional relationship between the translation unit 22 and the outer cylinder 91 of the entry guide 9 is known. An outer shape of the instrument manipulator 21 is known. A position of the distal end of the inner cylinder 92 relative to the outer cylinder 91 can be obtained based on a displacement amount by the guide advancing device 93 (or a detection value of a sensor provided in the guide advancing device 93). Therefore, based on a displacement amount of the instrument manipulator 21 in the insertion axial direction Xi by the translation unit 22 and a posture of the instrument manipulator 21, and a displacement amount of the inner cylinder 92 by the guide advancing device 93, the slave controller 3 can obtain an advancing amount of the instrument manipulator 21 from the entry guide 9. Similarly, the slave controller 3 can obtain an advancing amount of the endoscope manipulator 31 from the entry guide 9. Note that the advancing amount is a distance in the insertion axial direction Xi from the exit of the entry guide 9 (that is, the distal end of the inner cylinder 92) to the distal end of the instrument manipulator 21 (or the endoscope manipulator 31). Alternatively, the advancing amount is a distance in the insertion axial direction Xi from the exit of the entry guide 9 (that is, the distal end of the inner cylinder 92) to the shoulder 262 of the instrument manipulator 21 (or the endoscope manipulator 31).

The entry guide advancing operation may be performed in response to the input of the surgeon S. In this case, the slave controller 3 compares the advancing amount from the entry guide 9 of the instrument manipulator 21 and the endoscope manipulator 31 obtained as described above with a predetermined threshold. If the advancing amount exceeds the threshold, the slave controller 3 transmits guide advancement permission information to the master controller 8. The master controller 8 outputs information for permitting the entry guide advancing operation to at least one of the display device 73 and the manipulation input device 71 in response to the guide advancement permission information. The surgeon S can know that the inner cylinder 92 of the entry guide 9 can advance with respect to the instrument manipulator 21 and the endoscope manipulator 31 from the information that permits the entry guide advancing operation which is displayed on the display device 73 or provided, as a notification, to the manipulation input device 71 by vibration, voice, or the like.

Further, a movable range D is obtained based on the advancing amount of the instrument manipulator 21 and the endoscope manipulator 31 from the entry guide 9 (or a positional relationship between both the instrument manipulator 21 and the endoscope manipulator 31 and the entry guide 9). The movable range D may be, for example, the shorter one of a range from an exit of the entry guide 9 (that is, the distal end of the inner cylinder 92) to the shoulder 262 of the instrument manipulator 21 and a range from the exit of the entry guide 9 to the shoulder 262 of the endoscope manipulator 31. The slave controller 3 transmits information on the obtained movable range D to the master controller 8. An image processing unit 800 of the master controller 8 combines information on the movable range D with an endoscopic image to be displayed on the display device 73, and causes the display device 73 to display the movable range D together with the endoscopic image. In this manner, the surgeon S can visually recognize the information on the movable range D through the endoscopic image. Note that the information on the movable range D may be displayed on the display device 73 in at least one mode of a numerical value, a graph, and an image.

The manipulation input device 71 includes an entry guide advancing manipulation tool that receives inputs of an entry guide advancing operation manipulation. The entry guide advancing manipulation tool may be a button or a lever. Alternatively, one of the master manipulators 72L and 72R and the manipulation pedal 75 may have a function as the entry guide advancing manipulation tool. Upon receiving the guide advancement permission information, the surgeon S can operate the entry guide advancing manipulation tool to input the entry guide advancing operation manipulation. The input of the entry guide advancing operation manipulation may include a manipulation amount (displacement amount) of the entry guide 9 with respect to the instrument manipulator 21 and the endoscope manipulator 31.

An entry guide advancing operation command corresponding to the input entry guide advancing operation manipulation is transmitted from the master controller 8 to the slave controller 3. The slave controller 3 operates the guide advancing device 93 based on the entry guide advancing operation command. Here, the slave controller 3 may operate the guide advancing device 93 such that the inner cylinder 92 moves to the distal end of the movable range D. Alternatively, in a case where a manipulation amount is included in the entry guide advancing movement command, the slave controller 3 may operate the guide advancing device 93 so as to move the inner cylinder 92 in the movable range D in response to the manipulation amount.

(Operation of Surgery Manipulator 20 and Entry Guide 9 During Surgery)

The slave controller 3 operates the instrument manipulator 21 to change a position and a posture of the surgical instrument 28 inserted into the body cavity based on a movement command corresponding to input of a movement manipulation including an operation vector received by the console 7. The surgical assist robot 1 during surgery is controlled in a plurality of control modes including an instrument manipulation mode, an endoscope manipulation mode, and a guide manipulation mode. These control modes are stored in advance in the master controller 8. In the instrument manipulation mode, a position and a posture of the surgical instrument 28 are changed in response to input received by the manipulation input device 71. In the endoscope manipulation mode, a position and a posture of the endoscopic camera 33 change in response to the input received by the manipulation input device 71. In the guide manipulation mode, in response to the input received by the manipulation input device 71, a position and a posture of the entry guide 9 change while a relative positional relationship of between the entry guide 9 and the surgical instrument 28 and the endoscopic camera 33 is maintained. In the endoscope manipulation mode and the guide manipulation mode, the master controller 8 invalidates input of a manipulation for performing operation of emitting energy, such as anastomosis or suturing.

Switching: of a control mode is performed by one of the plurality of manipulation pedals 75. Methods (1) to (3) described below can be illustrated as methods of switching a control mode.

(1) An initial mode is set to an instrument manipulation mode, and when the manipulation pedal 75 is depressed for a predetermined time or more, the master controller 8 generates a command to switch from the instrument manipulation mode to the endoscope manipulation mode. When the manipulation pedal 75 is depressed for a predetermined time or less, the master controller 8 generates a command to switch from the endoscope manipulation mode to the guide manipulation mode. When the control mode is the endoscope manipulation mode or the guide manipulation mode, and the manipulation pedal 75 is depressed for a predetermined time or snore, the master controller 8 generates a command to switch from the endoscope manipulation mode or the guide manipulation mode to the instrument manipulation mode. The master controller 8 switches the control mode based on a generated mode switching command.

(2) An initial mode is set to an instrument manipulation mode, and when the manipulation pedal 75 is depressed for a predetermined time or more, the master controller 8 generates a command to switch from the instrument manipulation mode to the endoscope manipulation mode. When the control mode is the endoscope manipulation mode, and the manipulation pedal 75 is depressed for a predetermined time or more, the master controller 8 generates a command to switch from the endoscope manipulation mode to the instrument manipulation mode. When the manipulation pedal 75 is depressed for a predetermined time or less, the master controller 8 generates a command to switch from the instrument manipulation mode to the guide manipulation mode. When the control mode is the guide manipulation mode, and the manipulation pedal 75 is depressed for a predetermined time or less, the master controller 8 generates a command to switch from the guide manipulation mode to the instrument manipulation mode.

(3) An initial mode is set to an instrument manipulation mode, and when the manipulation pedal 75 is depressed for a predetermined time or more, the master controller 8 generates a command to switch from the instrument manipulation mode to the endoscope manipulation mode. When the control mode is the endoscope manipulation mode, and the manipulation pedal 75 is depressed for a predetermined time or more, the master controller 8 generates a command to switch from the endoscope manipulation mode to the guide manipulation mode. When the control mode is the endoscope manipulation mode, and the manipulation pedal 75 is depressed for a predetermined time or more, the master controller 8 generates a command to switch from the endoscope manipulation mode to the instrument manipulation mode.

In the above (1) to (3), the master controller 8 switches the control mode based on a generated control mode switching command. In any of the endoscope manipulation mode and the guide manipulation mode, an endoscope image displayed on the display device 73 changes in response to manipulation input by the surgeon S to the console 7. Therefore, as described above, commands to switch from the instrument manipulation mode to the endoscope manipulation mode and to switch from the instrument manipulation mode to the guide manipulation mode are input using the same manipulation pedal 75.

Figure 8:
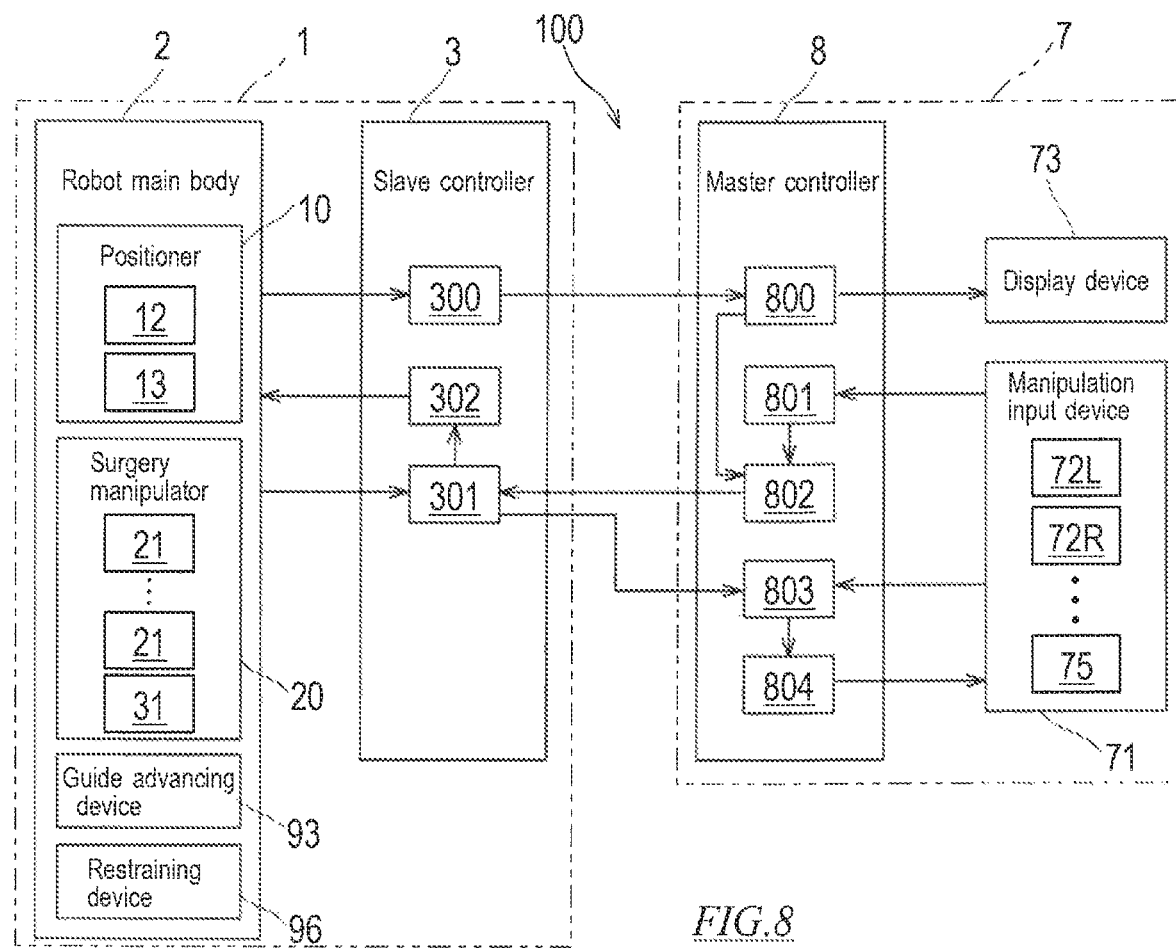
FIG. 8 is a block diagram showing a configuration of a control system of the surgical system showing flow of processing in an instrument manipulation mode.

FIG. 8 is a block diagram showing a configuration of the control system of the surgical system 100 showing flow of processing in the instrument manipulation mode. As shown in FIG. 8, in the instrument manipulation mode, the surgeon S inputs manipulations of the movement of the end effector provided at a distal end of the slave manipulator by directly moving the manipulation unit provided at a distal end of the master manipulators 72L and 72R while checking an affected area on an endoscopic image displayed on the display device 73. The slave manipulator is, for example, the instrument manipulator 21 associated with the master manipulators 72L and 72R by the manipulation of the manipulation pedal 75, and the end effector is the surgical instrument 28. Among the plurality of instrument manipulators 21 included in the robot main body 2, instrument manipulators 21 that are not associated with the master manipulators 72L and 72R as slave manipulators apply a brake to the servomotor that operates each joint so as not to change a position and a posture. A servomotor with a mechanical brake is preferably employed as a servomotor for driving a joint of the instrument manipulator 21.

The master controller 8 includes an image processing unit 800, an input processing unit 801, a movement command generation unit 802, a master position command generation unit 803, and a master driver 804. The input processing unit 801 obtains each joint position from the rotation sensor provided corresponding to each joint of the master manipulators 72L and 72R, and obtains a position and a speed (moving speed) of the manipulation unit from each joint position. The movement command generation unit 802 uses information displayed on the display device 73 generated by the image processing unit 800, that is, visibility information of the surgeon S to convert a position and a speed of the manipulation unit acquired from the input processing unit 801 into an orthogonal coordinate system and further convert the orthogonal coordinate system into a predetermined scale so as to generate a movement command including a position and a speed. The generated movement command is transmitted to the slave controller 3.

The slave controller 3 includes an image acquisition unit 300, a slave position command generation unit 301, and a slave driver 302. The image acquisition unit 300 acquires image data captured by the endoscopic camera 33 and transmits the image data to the image processing unit 800 of the roaster controller 8. The slave position command generation unit 301 generates a slave position command from an acquired movement command based on various types of restriction information set in advance. Restriction of a movement range set in advance, restriction of a movement speed, or the like is applied to the slave position command. The slave driver 302 obtains each joint position from the rotation sensor provided corresponding to each joint of the slave manipulator. The slave driver 302 obtains a drive torque for each joint based on the slave position command and each joint position, and supplies a current corresponding to the drive torque to a servomotor that drives the joint. In this manner, the slave manipulator operates in response to the movement of the manipulation unit of the master manipulators 72L and 72R.

On the other hand, the slave position command generated by the slave position corer and generation unit 301 is transmitted to the master position command generation unit 803 of the master controller 8. Based on the acquired slave position command and the movement command which is acquired from the movement command generation unit 802, the master position command generation unit 803 generates a master position command such that the manipulation unit of the master manipulators 72L and 72R is at the position and in the posture each corresponding to the end effector of the slave manipulator. The master position command includes a reaction force described later. The master driver 804 obtains a drive torque for each joint based on the master position command and each joint position of the master manipulators 72L and 72R, and supplies a current corresponding to the drive torque to a servomotor that drives the joint. In this manner, operation is performed in such a mangier that the position and the posture of the manipulation unit of the master manipulators 72L and 72R correspond to the position and the posture of the end effector of the slave manipulator.

<Endoscope Manipulation Mode>

In the endoscope manipulation mode, a guide manipulation unit for receiving input of a movement manipulation of the endoscopic camera 33 is the master manipulators 72L and 72R. In the endoscope manipulation mode, the surgeon S directly moves the manipulation unit at the distal end of the master manipulators 72L and 72R while checking the affected area on an endoscopic image displayed on the display device 73, so as to input manipulations regarding the movements of a position and a posture of the endoscopic camera 33. The master controller 8 restricts operation of two of the master manipulators 72L and 72R such that relative postures of two of the master manipulators 72L and 72R are maintained in the endoscope manipulation mode.

The input processing unit 801 of the master controller 8 obtains each joint position from the rotation sensor provided corresponding to each joint of the master manipulators 72L and 72R, and obtains a position and a speed (moving speed) of the manipulation unit from each joint position.

The movement command generation unit 802 of the master controller 8 uses information displayed on the display device 73 generated by the image processing unit 800, that is, visibility information of the surgeon S to convert a position and a speed of the manipulation unit acquired from the input processing unit 801 into an orthogonal coordinate system so as to generate a movement command including a position and a speed. The generated movement command is transmitted to the slave controller 3. Here, the movement command generation unit 802 generates an advancing movement command for the endoscopic camera 33 in response to operation in which the surgeon pulls the master manipulators 72L and 72R toward the surgeon, that is, the surgeon moves the master manipulators 72L and 72R in a rear direction B, generates a retracting movement command for the endoscopic camera 33 in response to operation in which the surgeon pushes the master manipulators 72L and 72R in a forward direction F, generates a movement command to the right and left for the endoscopic camera 33 in response to operation in which the surgeon moves the master manipulators 72L and 72R in a left direction L and a right direction R, and generates a rotational movement command for the endoscopic camera 33 in response to operation in which the surgeon rotates the master manipulators 72L and 72R.

The slave controller 3 operates the endoscope manipulator 31, which is a slave manipulator, based on an acquired movement command, as in the case of the above-described instrument manipulation mode. In this manner, the endoscope manipulator 31 operates in response to the movement of the manipulation unit of the master manipulators 72L and 72R.

<Guide Manipulation Mode>

Figure 9:
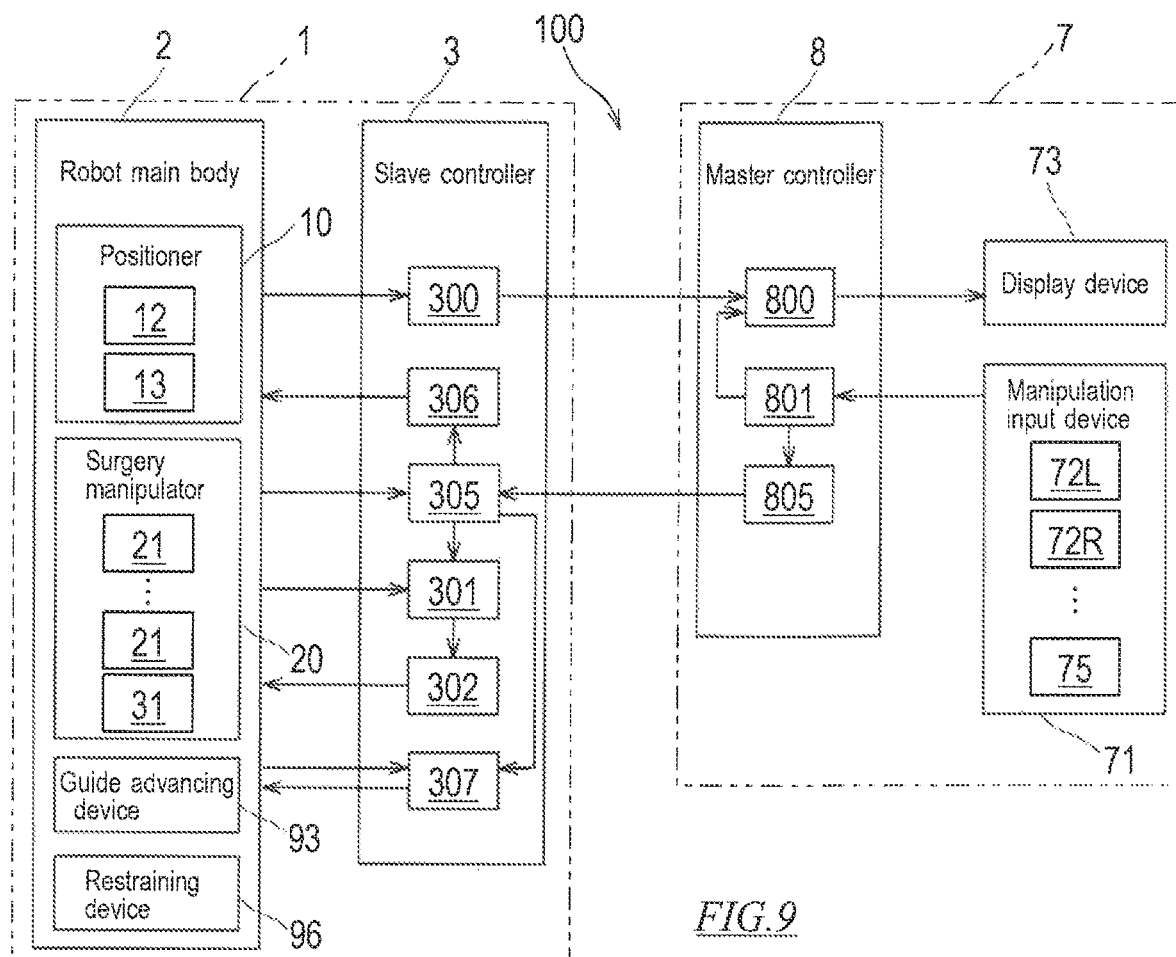
FIG. 9 is a block diagram showing a configuration of the control system of the surgical system showing flow of processing in a guide manipulation mode.

FIG. 9 is a block diagram showing a configuration of the control system of the surgical system 100 showing flow of processing in the guide manipulation mode. In the guide manipulation mode, a guide manipulation unit for receiving input of a movement command of the entry guide 9 is the master manipulators 72L and 72R. As shown in FIG. 9, in the guide manipulation mode, the surgeon S directly moves the manipulation unit at the distal end of the master manipulators 72L and 72R while checking the affected area on an endoscopic image displayed on the display device 73, so as to command movement of a position and a posture of the distal end of the entry guide 9. The master controller 8 restricts operation of two of the master manipulators 72L and 72R such that relative postures of two of the master manipulators 72L and 72R are maintained in the guide manipulation mode.

The input processing unit 801 of the master controller 8 obtains each joint position from the rotation sensor provided corresponding to each joint of the master manipulators 72L and 72R, and obtains a position and a speed (moving speed) of the manipulation unit from each joint position.

A guide movement command generation unit 805 of the master controller 8 uses information displayed on the display device 73 generated by the image processing unit 800, that is, visibility information of the surgeon S to convert a position and a speed of the manipulation unit acquired from the input processing unit 801 into an orthogonal coordinate system so as to generate a movement command including a position and a speed. The generated guide movement command is transmitted to the slave controller Here, the guide movement command generation unit 805 generates an advancing movement command for the inner cylinder 92 in response to operation in which the surgeon pulls the master manipulators 72L and 72R toward the surgeon, that is, the surgeon moves the master manipulators 72L and 72R in the rear direction B, generates a retracting movement command for the inner cylinder 92 in response to operation in which the surgeon pushes the master manipulators 72L and 72R in the forward direction F, generates a movement command to the right and left for the inner cylinder 92 in response to operation in which the surgeon moves the master manipulators 72L and 72R in the left direction L and the right direction R, and generates a rotational movement command for the inner cylinder 92 in response to operation in which the surgeon rotates the master manipulators 72L and 72R. As described above, manipulation of the surgeon S is simplified by employing a common manipulation method in the guide manipulation mode and the endoscope manipulation mode involving movement of the endoscopic camera 33.

A guide position command generation unit 305 of the slave controller 3 generates a guide position command from an acquired guide movement command. In a case where the guide movement command is an advancing movement command or a retracting movement command for the inner cylinder 92, the guide position command generation unit 305 outputs a guide position command to a guide driver 306 and the slave position command generation unit 301. The guide driver 306 obtains a position of the distal end of the inner cylinder 92 from a position sensor provided in the guide advancing device 93. The guide driver 306 obtains a drive torque of the guide advancing device 93 based on the position of the distal end of the inner cylinder 92 and the guide position command, and supplies a current corresponding to the drive torque to a servomotor included in the guide advancing device 93. The slave position command generation unit 301 generates a slave position command from the acquired guide position command such that a relative positional relationship between the inner cylinder 92 and all of the instrument manipulators 21 and the endoscope manipulator 31 inserted in the inner cylinder 92 is maintained. The slave driver 302 obtains each joint position from the rotation sensor provided corresponding to each joint of the slave manipulator (that is, the instrument manipulator 21 and the endoscope manipulator 31). Then, the slave driver 302 obtains a drive torque for each joint based on the slave position command and each joint position, and supplies a current corresponding to the drive torque to a servomotor that drives the joint. In this manner, the inner cylinder 92 moves forward and backward relative to the outer cylinder 91 while a relative positional relationship between the inner cylinder 92 and all the instrument manipulators 21 and the endoscope manipulator 31 inserted in the inner cylinder 92 is maintained.

On the other hand, in a case where the guide movement command is a movement command to the right and left of the inner cylinder 92 and a rotation command, the guide position command generation unit 305 outputs a guide position command to a positioner driver 307. The positioner driver 307 obtains a position of the entry guide support portion 14b from a position sensor provided for each joint of the vertical articulated manipulator 13, and, from this position, obtains a position of the distal end of the inner cylinder 92. Then, based on the position of the distal end of the inner cylinder 92 and the guide position command, the positioner driver 307 obtains a drive torque for each joint of the vertical articulated manipulator 13 and supplies a current corresponding to the drive torque to a servomotor that drives the joint. In this manner, the entry guide 9 changes postures of the instrument manipulator 21 and the endoscope manipulator 31 together with the support frame 14 supporting the instrument manipulator 21 and the endoscope manipulator 31.

(Extraction Operation for Patient Tissue T by Instrument Manipulator 21)

Figure 11:
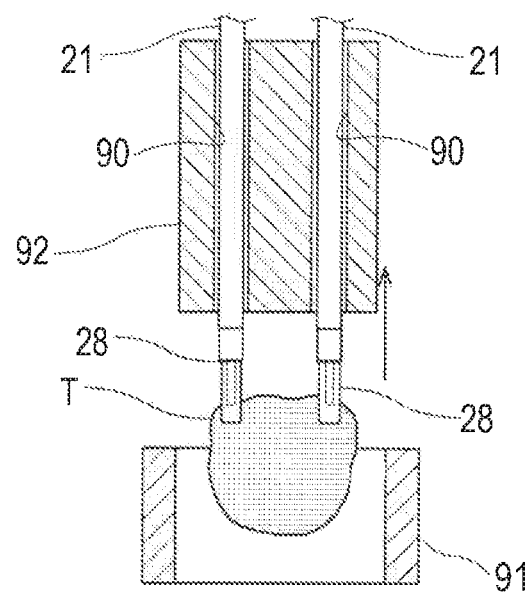
FIG. 11 is a diagram showing a state in which the inner cylinder of the entry guide is pulled out of an outer cylinder.

During surgery, a patient tissue T excised in a body cavity is extracted to the outside of the body cavity through an opening provided in the entry guide 9. In the entry guide 9 according to the present embodiment, the inner cylinder 92 can be pulled out from the outer cylinder 91. As shown in FIG. 11, while the patient tissue T in the body cavity is held by the surgical instrument 28 of the instrument manipulator 21, the inner cylinder 92 is pulled out from the outer cylinder 91 together with the instrument manipulator 21 and the endoscope manipulator 31 inserted into the inner cylinder 92. In this manner, the patient tissue T held by the surgery manipulator 20 can be extracted out of the body cavity.

The manipulation input device 71 includes a manipulation tool that receives input of a tissue extraction manipulation. The master controller 8 transmits a tissue extraction command corresponding to the input of the tissue extraction manipulation to the slave controller 3. Based on the tissue extraction command, the slave controller 3 operates the translation unit 22 to retract the surgical instrument 28 and the endoscopic camera 33 from a body cavity in the insertion axial direction Xi while keeping the instrument manipulator 21 and the endoscope manipulator 31 restrained in the inner cylinder 92. Here, the surgical instrument 28 and the endoscopic camera 33 simultaneously move in the insertion axial direction Xi. The surgical instrument 28 and the endoscopic camera 33 may move at the same speed in the insertion axial direction Xi. In this manner, the inner cylinder 92 is pulled out from the outer cylinder 91 together with the instrument manipulator 21 and the endoscope manipulator 31 inserted into the inner cylinder 92.

Figure 12:
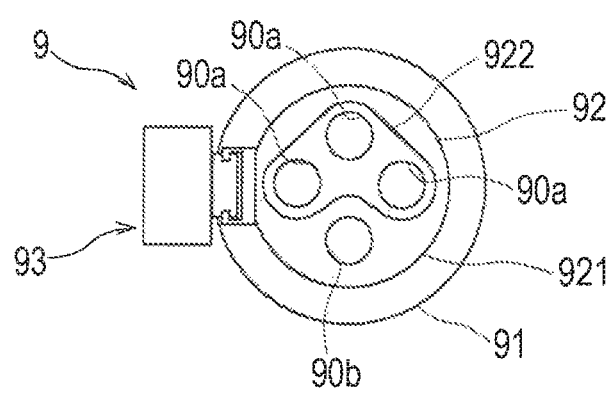
FIG. 12 is a plan view of the entry guide according to a variation.

Although the entire inner cylinder 92 is pulled out from the outer cylinder 91 in the above description, a portion of the inner cylinder 92 may be pulled out from another portion. For example, as shown in FIG. 12, the inner cylinder 92 may be configured with a frame portion 921 and an extraction portion 922. The frame portion 921 is provided with a guide bore 90b through which the endoscope manipulator 31 described later is inserted. The extraction portion 922 is provided with a guide bore 90a into which the instrument manipulator 21 described later is inserted. In this configuration, the patient tissue T held by the surgical instrument 28 of the instrument manipulator 21 can be extracted from the body cavity by pulling out the extraction portion 922 from the frame portion 921 while leaving the frame portion 921 in the outer cylinder 91.

As described above, a cross-sectional area of a hole formed in the outer cylinder 91 by the removal of the inner cylinder 92 from the outer cylinder 91 is larger than a cross-sectional area of the guide bore 90. Similarly, a cross-sectional area of a hole formed in the frame portion 921 by the removal of the extraction portion 922 from the frame portion 921 is larger than a cross-sectional area of the guide bore 90. Therefore, the inner cylinder 92, part or whole of which can be pulled out from the entry guide 9, is useful in a case where the relatively large patient tissue T is extracted from the body cavity. Note that, in the above description, the inner cylinder 92 is pulled out from the outer cylinder 91 by the operation of the instrument manipulator 21. However, the inner cylinder 92 may be manually pulled out from the outer cylinder 91. Similarly, the extraction portion 922 may be pulled out from the inner cylinder 92.

As described above, the surgical system 100 according to the present embodiment includes the surgical assist robot 1 having the robot main body 2 and the slave controller 3, and the console 7 that is communicably connected to the slave controller 3, acquires input from the surgeon S, and transmits a command corresponding to the input to the slave controller 3. The robot main body 2 includes the entry guide 9 including the inner cylinder 92 extending in the insertion axial direction Xi, the outer cylinder 91 in which the inner cylinder 92 is inserted in the insertion axial direction Xi, and the guide advancing device 93 that displaces the inner cylinder 92 in the insertion axial direction Xi with respect to the outer cylinder 91, the positioner 10 as an entry guide support device for supporting the entry guide 9, and at least one manipulator (the instrument manipulator 21 and the endoscope manipulator 31) that has an end effector (the surgical instrument 28 or the endoscopic camera 33) provided at a distal end and is inserted into the inner cylinder 92. The slave controller 3 controls the robot main body 2 to perform entry guide advancing operation. The entry guide advancing operation is operation to cause the inner cylinder 92 to advance toward the end effector within the predetermined movable range D along the insertion axial direction Xi with respect to the outer cylinder 91 while maintaining a position and a posture of the end effector that has advanced from the entry guide 9.

Similarly, the method for controlling the surgical system 100 according to the present embodiment includes the steps of: receiving input of a body cavity insertion manipulation via the console 7; operating a manipulator such that an end effector advances from the entry guide 9 in response to the input of the body cavity insertion manipulation; and operating the entry guide 9 so as to perform the entry guide advancing operation to cause the inner cylinder 92 to advance toward the end effector within a predetermined movable range along the insertion axial direction Xi with respect to the outer cylinder 91 while maintaining a position and a posture of the end effector that has advanced from the entry guide 9.

According to the above surgical system 100 and the method for controlling the surgical system 100, the distal end of the manipulators 21 and 31 and the distal end of the entry guide 9 (that is, the distal end of the inner cylinder 92) approach by the entry guide advancing operation. In other words, a length of the manipulators 21 and 31 advancing from the exit of the entry guide 9 is shortened. Therefore, shaking and deformation of a portion of the manipulators 21 and 31 advancing from the exit of the entry guide 9 can be reduced, and the positional accuracy of the end effectors 28 and 33 can be improved.

In the above, the slave controller 3 may cause the robot main body 2 to perform the entry guide advancing operation when the advancing amount in the insertion axial direction Xi from the exit of the entry guide 9 of the end effectors 28 and 33 exceeds a predetermined threshold.

Similarly, in the step of operating the entry guide 9 in the method for controlling the surgical system 100, the entry guide advancing operation may be performed when the advancing amount in the insertion axial direction Xi from the exit of the entry guide 9 of the end effector exceeds a predetermined threshold.

In this manner, the entry guide advancing operation is automatically performed without the surgeon S manipulating, and the advancing amount from the exit of the entry guide 9 of the manipulators 21 and 31 is appropriately adjusted.

Alternatively, the configuration may be such that the console 7 has the manipulation input device 71 that receives input of a manipulation to the surgical assist robot 1 from the surgeon S and the master controller 8, the master controller 8 transmits a guide movement command corresponding to the input received by the manipulation input device 71 to the slave controller 3, and the slave controller 3 causes the robot main body 2 to perform the entry guide advancing operation if the advancing amount in the insertion axial direction Xi from the exit of the entry guide 9 of the end effectors 28 and 33 exceeds a predetermined threshold in response to the guide movement command.

Similarly, the configuration may be such that the method for controlling the surgical system 100 further includes the step of receiving input of a guide movement manipulation via the manipulation input device 71, and, in the step of operating the entry guide 9, when the input of the guide movement manipulation is received, the entry guide advancing operation is performed if the advancing amount in the insertion axial direction Xi from the exit of the entry guide 9 of the end effector exceeds a predetermined threshold.

In this manner, the entry guide advancing operation is performed based on a input of the surgeon S.

In the above, the configuration may be such that the manipulators 21 and 31 include the endoscope manipulator 31 having the endoscopic camera 33 provided at the distal end, the console 7 includes the display device 73 that displays an endoscopic image, the slave controller 3 transmits information related to the movable range D to the master controller 8, and the master controller 8 causes the display device 73 to display information related to the movable range D together with the endoscopic image.

In this manner, the surgeon S can know the movable range D by seeing the movable range D displayed on the display device 73 together with the endoscopic image.

Further, in the above, the configuration may be such that if the advancing amount in the insertion axial direction Xi of the end effectors 33 and 38 from the entry guide 9 exceeds a predetermined threshold, the slave controller 3 transmits the guide advancement permission information to the master controller 8, and the master controller 8 outputs information for permitting the entry guide advancing operation to at least one of the display device 73 and the manipulation input device 71 in response to the guide advancement permission information.

In this manner, the surgeon S can know that the entry guide advancing operation is possible through the display device 73 and the manipulation input device 71.

Further, in the surgical system 100 according to the present embodiment, the entry guide 9 forms at least one of the guide bores 90 into which the manipulators 21 and 31 are inserted, and includes an extraction portion (the extraction portion 922 or the entire inner cylinder 92) that can be extracted from another portion of the entry guide 9 in the insertion axial direction Xi.

As described above, the patient tissue T can be extracted out of the body cavity by pulling out the extraction portion (the extraction portion 922 or the entire inner cylinder 92) of the entry guide 9 from remaining part of the entry guide 9 together with the instrument manipulator 21 holding the patient tissue T. A cross-sectional area of a hole formed in the remaining part of the entry guide 9 by the removal of the extraction portion (the extraction portion 922 or the entire inner cylinder 92) of the entry guide 9 is larger than a cross-sectional area of the guide bore 90. Accordingly, it is possible to extract a relatively large patient tissue T from the body cavity.

Further, in the surgical system 100 according to the present embodiment, the manipulators 21 and 31 include the instrument manipulator 21 having the surgical instrument 28 provided at the distal end and the endoscope manipulator 31 having the endoscopic camera 33 provided at the distal end, and a plurality of control modes are specified, the control modes including the instrument manipulation mode for changing a position and a posture of the surgical instrument 28 in response to the input received by the console 7, the endoscope manipulation mode for changing a position and a posture of the endoscopic camera 33 in response to the input received by the console 7, and a guide manipulation mode for changing a position and a posture of the distal end of the entry guide 9 in response to the input received by the console 7. Then, in the guide manipulation mode, the slave controller 3 operates the robot main body 2 such that a relative positional relationship between the inner cylinder 92, the instrument manipulator 21, and the endoscope manipulator 31 is maintained.

Similarly, in the method for controlling the surgical system 100 according to the present embodiment, operation of the robot main body 2 has a plurality of control modes including an instrument manipulation mode for changing a position and a posture of the surgical instrument 28 in response to the input received by the console 7, an endoscope manipulation mode for changing a position and a posture of the endoscopic camera 33 in response to the input received by the console 7, and a guide manipulation mode for changing a position and a posture of the distal end of the entry guide 9 in response to the input received by the console 7. Then, in the guide manipulation mode, a relative positional relationship between the inner cylinder 92, the instrument manipulator 21, and the endoscope manipulator 31 is maintained.

In this guide manipulation mode, the inner cylinder 92, the instrument manipulator 21, and the endoscope manipulator 31 can be moved to a next surgical position while a relative positional relationship of them is maintained.

In the above, the console 7 includes a manipulation tool (the master manipulators 72L and 72R) that functions as a guide manipulation unit that receives input of a movement manipulation for the entry guide 9 and an endoscope manipulation unit that receives input of a movement manipulation for the endoscopic camera 33. Then, in the guide manipulation mode, the console 7 generates an advancing movement command for the inner cylinder 92 in response to operation of the surgeon S pulling the manipulation tool toward the surgeon S, generates a retracting movement command for the inner cylinder 92 in response to operation of the surgeon S pushing the manipulation tool forward, generates a right and left movement command for the inner cylinder 92 in response to operation of the surgeon S moving the manipulation tool to the left and right, generates a rotation movement command for the inner cylinder 92 in response to operation of the surgeon S rotating the manipulation tool, and transmits the generated command to the slave controller 3. Further, in the endoscope manipulation mode, the console 7 generates an advancing movement command for the endoscopic camera 33 in response to operation of the surgeon S pulling the manipulation tool toward the surgeon S, generates a retracting movement command for the endoscopic camera 33 in response to operation of the surgeon S pushing the manipulation tool forward, generates a right and left movement command for the endoscopic camera 33 in response to operation of the surgeon S moving the manipulation tool to the left and right, generates a rotation movement command for the endoscopic camera 33 in response to operation of the surgeon S rotating the manipulation tool, and transmits the generated command to the slave controller 3.

Similarly, in the method for controlling the surgical system 100, in the guide manipulation mode, the console generates an advancing movement command for the inner cylinder 92 in response to operation of the surgeon S pulling the manipulation tool toward the surgeon S, generates a retracting movement command for the inner cylinder 92 in response to operation of the surgeon S pushing the manipulation tool forward, generates a right and left movement command for the inner cylinder 92 in response to operation of the surgeon S moving the manipulation tool to the left and right, and generates a rotation movement command for the inner cylinder 92 in response to operation of the surgeon S rotating the manipulation tool. Further, in the endoscope manipulation mode, the console 7 generates an advancing movement command for the endoscopic camera 33 in response to operation of the surgeon S pulling the manipulation tool toward the surgeon S, generates a retracting movement command for the endoscopic camera 33 in response to operation of the surgeon S pushing the manipulation tool forward, generates a right and left movement command for the endoscopic camera 33 in response to operation of the surgeon S moving the manipulation tool to the left and right, and generates a rotation movement command for the endoscopic camera 33 in response to operation of the surgeon S rotating the manipulation tool.

As described above, manipulation of the surgeon S is simplified by employing a common manipulation method in the guide manipulation mode and the endoscope manipulation mode involving movement of the endoscopic camera 33.

Further, in the above, the console 7 has a single manipulation tool (the manipulation pedal 75) that receives input of a manipulation to switch the control mode to the endoscope manipulation mode and input of a manipulation to switch the control mode to the guide manipulation mode.

As described above, since the manipulation tool for switching the control mode to the guide manipulation mode and the endoscope manipulation mode accompanied by movement of the endoscopic camera 33 is common, the manipulation of the surgeon S is simplified.

Further, in the surgical assist robot 1 according to the present embodiment, the robot main body 2 includes two of the instrument manipulators 21, and the console 7 has two of the master manipulators 72L and 72R that receive input of a movement manipulation for a position and a posture of the surgical instrument 28 corresponding to the two instrument manipulators 21. Then, in the guide manipulation mode, operation of the two master manipulators 72L and 72R is restricted such that relative postures of the two master manipulators 72L and 72R are maintained.

Similarly, in the method for controlling the surgical assist robot 1 according to the present embodiment, the robot main body 2 includes two of the instrument manipulators 21 and the console 7 has two of the master manipulators 72L and 72R that receive input of a movement manipulation for a position and a posture of the surgical instrument 28 in a manner corresponding to the two instrument manipulators 21. In the guide manipulation mode, operation of two of the master manipulators 72L and 72R is restricted such that relative postures of the two master manipulators 72L and 72R are maintained.

In this manner, matching between a positional relationship of the pair of surgical instruments 28 and a positional relationship of the manipulation units of the pair of master manipulators 72L and 72R can be omitted after the entry guide 9 is moved by the guide manipulation mode.

Although the preferred embodiments of the present invention are described above, modifications of details of the specific structure and/or function details of the above-described embodiments may be included in the present invention without departing from the spirit of the present invention.

What is claimed is:

1. A surgical system comprising:
   a surgical assist robot having a robot main body and a slave controller; and
   a console that is communicably connected to the slave controller and configured to acquire input from a surgeon and transmit a command corresponding to the input to the slave controller, wherein
   the robot main body has:
   an entry guide including an inner cylinder extending in an insertion axial direction, an outer cylinder in which the inner cylinder is inserted in the insertion axial direction, and a guide advancing device configured to displace the inner cylinder in the insertion axial direction with respect to the outer cylinder;
   an entry guide support device configured to support the entry guide; and
   at least one manipulator that has an end effector provided at a distal end and is inserted into the inner cylinder, the slave controller controls the robot main body to perform an entry guide advancing operation, in which the inner cylinder is caused to advance toward the end effector within a predetermined movable range along the insertion axial direction with respect to the outer cylinder while a position and a posture of the end effector that has advanced from the entry guide are maintained, and the slave controller causes the robot main body to perform the entry guide advancing operation when an advancing amount of the end effector, in the insertion axial direction, relative to an exit of the entry guide exceeds a predetermined threshold.

2. The surgical system according to claim 1, wherein
the console has a manipulation input device that receives input of a manipulation to the surgical assist robot from the surgeon, and a master controller, the master controller transmits a guide movement command corresponding to the input received by the manipulation input device to the slave controller, and the slave controller causes the robot main body to perform the entry guide advancing operation when the advancing amount exceeds the predetermined threshold based on the guide movement command.

3. The surgical system according to claim 2, wherein
the at least one manipulator includes an endoscope manipulator having an endoscopic camera provided at a distal end of the endoscope manipulator, the console includes a display device that displays an endoscopic image, the slave controller transmits information related to the movable range to the master controller, and the master controller causes the display device to display information related to the movable range together with the endoscopic image.

4. The surgical system according to claim 3, wherein
the slave controller transmits guide advancement permission information to the master controller when the advancing amount exceeds the predetermined threshold, and the master controller outputs information for permitting the entry guide advancing operation to at least one of the display device and the manipulation input device in response to the guide advancement permission information.

5. The surgical system according to claim 1, wherein entry guide forms at least one guide bore into which the at least one manipulator is inserted, and includes an extraction portion which can be extracted in the insertion axial direction from another portion of the entry guide.

6. The surgical system according to claim 1, wherein
the at least one manipulator includes a first instrument manipulator having a surgical instrument provided at a distal end of the first instrument manipulator and includes an endoscope manipulator having an endoscopic camera provided at a distal end of the endoscope manipulator, a plurality of control modes are specified, the control modes including an instrument manipulation mode for changing a position and a posture of the surgical instrument based on a command from the console, an endoscope manipulation mode for changing a position and a posture of the endoscopic camera based on a command from the console, and a guide manipulation mode for changing a position and a posture of a distal end of the entry guide based on a command from the console, and in the guide manipulation mode, the slave controller operates the robot main body such that a positional relationship between the inner cylinder, the first instrument manipulator, and the endoscope manipulator is maintained.

7. The surgical system according to claim 6, wherein
the console has a manipulation tool that functions as a guide manipulation unit configured to receive input of a manipulation for the entry guide and that functions as an endoscope manipulation unit configured to receive input of a manipulation for the endoscopic camera, in the guide manipulation mode, the console generates an advancing movement command for the inner cylinder in response to operation of the surgeon pulling the manipulation tool toward the surgeon, generates a retracting movement command for the inner cylinder in response to operation of the surgeon pushing the manipulation tool forward, generates a right movement command for the inner cylinder in response to operation of the surgeon moving the manipulation tool a right direction, generates a left movement command for the inner cylinder in response to operation of the surgeon moving the manipulation tool in a left direction, generates a rotation movement command for the inner cylinder in response to operation of the surgeon rotating the manipulation tool, and transmits a generated command to the slave controller, and in the endoscope manipulation mode, the console generates an advancing movement command for the endoscopic camera in response to operation of the surgeon pulling the manipulation tool toward the surgeon, generates a retracting movement command for the endoscopic camera in response to operation of the surgeon pushing the manipulation tool forward, generates a right movement command for the endoscopic camera in response to operation of the surgeon moving the manipulation tool to the right, generates a left movement command for the endoscopic camera in response to operation of the surgeon moving the manipulation tool to the left, generates a rotation movement command for the endoscopic camera in response to operation of the surgeon rotating the manipulation tool, and transmits a generated command to the slave controller.

8. The surgical system according to claim 6, wherein the console has a single manipulation tool that receives input of a manipulation to switch a current control mode to the endoscope manipulation mode and that receives input of a manipulation to switch the current control mode to the guide manipulation mode.

9. The surgical system according to claim 6, wherein
the robot main body further includes a second instrument manipulator, the second instrument manipulator being identical to the first instrument manipulator, and the console has two master manipulators that receive input of a manipulation for a position and a posture of the surgical instrument in a manner corresponding to the first and second instrument manipulators, and the console restricts, in the guide manipulation mode, operation of the two master manipulators such that postures of the two master manipulators are maintained.

10. A method for controlling a surgical system including a surgical assist robot including a robot main body and a console that receives input by a surgeon, the robot main body having:
an entry guide including an inner cylinder extending in an insertion axial direction, an outer cylinder in which the inner cylinder is inserted in the insertion axial direction, and a guide advancing device configured to displace the inner cylinder in the insertion axial direction with respect to the outer cylinder;

an entry guide support device configured to support the entry guide; and at least one manipulator that has an end effector provided at a distal end and is inserted into the inner cylinder, the method comprising the steps of:

receiving input of a body cavity insertion manipulation via the console;

operating the at least one manipulator, such that the end effector advances from the entry guide, in response to the input of the body cavity insertion manipulation; and operating the entry guide to perform an entry guide advancing operation, in which the inner cylinder is caused to advance toward the end effector within a predetermined movable range along the insertion axial direction with respect to the outer cylinder while a position and a posture of the end effector that has advanced from the entry guide are maintained, wherein the entry guide advancing operation is performed when an advancing amount of the end effector, in the insertion axial direction, relative to an exit of the entry guide exceeds a predetermined threshold.

11. The method for controlling the surgical system according to claim 10, wherein the console has a manipulation input device for receiving input of a manipulation from the surgeon to the surgical assist robot, the method further comprising a step of receiving input of a guide movement manipulation via the manipulation input device, wherein in the step of operating the entry guide, the entry guide advancing operation is performed when the advancing amount exceeds the predetermined threshold when the input of the guide movement manipulation is received.

12. The method for controlling the surgical system according to claim 10, wherein the at least one manipulator includes an endoscope manipulator having an endoscopic camera provided at a distal end of the endoscope manipulator, and the console includes a display device configured to display information on the movable range together with an endoscopic image.

13. The method for controlling the surgical system according to claim 12, wherein the console further includes a manipulation input device that receives input of a manipulation from the surgeon to the surgical assist robot, the method further including a step of outputting information for permitting the entry guide advancing operation to at least one of the display device and the manipulation input device when the advancing amount exceeds the predetermined threshold.

14. The method for controlling the surgical system according to claim 10, wherein the entry guide forms at least one guide bore into which the at least one manipulator is inserted, and includes an extraction portion which can be extracted in the insertion axial direction from another portion of the entry guide.

15. The method for controlling the surgical system according to claim 10, wherein the at least one manipulator includes a first instrument manipulator having a surgical instrument provided at a distal end of the first instrument manipulator and includes an endoscope manipulator having an endoscopic camera provided at a distal end of the endoscope manipulator, operation of the robot main body has a plurality of control modes including an instrument manipulation mode for changing a position and a posture of the surgical instrument based on a command from the console, an endoscope manipulation mode for changing a position and a posture of the endoscopic camera based on a command from the console, and a guide manipulation mode for changing a position and a posture of a distal end of the entry guide based on a command from the console, and in the guide manipulation mode, a positional relationship between the inner cylinder, the first instrument manipulator, and the endoscope manipulator is maintained.

16. The method for controlling the surgical system according to claim 15, wherein the console has a manipulation tool that functions as a guide manipulation unit configured to receive input of a movement manipulation for the entry guide and that functions as an endoscope manipulation unit configured to receive input of a movement manipulation for the endoscopic camera, in the guide manipulation mode, the console generates an advancing movement command for the inner cylinder in response to operation of the surgeon pulling the manipulation tool toward the surgeon, generates a retracting movement command for the inner cylinder in response to operation of the surgeon pushing the manipulation tool forward, generates a right movement command for the inner cylinder in response to operation of the surgeon moving the manipulation tool to the right, generates a left movement command for the inner cylinder in response to operation of the surgeon moving the manipulation tool to the left, and generates a rotation movement command for the inner cylinder in response to operation of the surgeon rotating the manipulation tool, and in the endoscope manipulation mode, the console generates an advancing movement command for the endoscopic camera in response to operation of the surgeon pulling the manipulation tool toward the surgeon, generates a retracting movement command for the endoscopic camera in response to operation of the surgeon pushing the manipulation tool forward, generates a right movement command for the endoscopic camera in response to operation of the surgeon moving the manipulation tool in a right direction, generates a left movement command for the endoscopic camera in response to operation of the surgeon moving the manipulation tool in a left direction, and generates a rotation movement command for the endoscopic camera in response to operation of the surgeon rotating the manipulation tool.

17. The method for controlling the surgical system according to claim 15, wherein the console has a single manipulation tool that receives input of a manipulation to switch a current control mode to the endoscope manipulation mode and that receives input of a manipulation to switch the current control mode to the guide manipulation mode.

18. The method for controlling the surgical system according to claim 15, wherein the robot main body further includes a second instrument manipulator, the second instrument manipulator being identical to the first instrument manipulator, and the console has two master manipulators that receive input of manipulations regarding movements for a position and a posture of the surgical instrument in a manner corresponding to the first and second instrument manipulators, and the console restricts, in the guide manipulation mode, operation of the two master manipulators such that postures of the two master manipulators are maintained.

* * * * *